United States Patent [19]

Tretinyak

[11] 4,403,617
[45] Sep. 13, 1983

[54] BIOPSY NEEDLE

[75] Inventor: Carl W. Tretinyak, Rochester, Minn.

[73] Assignee: Waters Instruments, Inc., Rochester, Minn.

[21] Appl. No.: 299,981

[22] Filed: Sep. 8, 1981

[51] Int. Cl.³ .............................................. A61B 10/00
[52] U.S. Cl. ................................... 128/754; 128/310; 604/164; 604/170
[58] Field of Search ..................... 128/749, 751–754, 128/310, 347, 221; 604/46, 47, 164, 166, 170, 272

[56] References Cited

U.S. PATENT DOCUMENTS

| | | | |
|---|---|---|---|
| 1,147,408 | 7/1915 | Kells | 128/347 |
| 2,516,492 | 7/1950 | Turkel | 128/751 |
| 3,175,554 | 3/1965 | Stewart | 128/754 |
| 3,477,423 | 11/1969 | Griffith | 128/754 |
| 3,605,721 | 9/1971 | Hallac | 128/754 |
| 3,788,119 | 1/1974 | Arrigo | 128/221 X |
| 3,788,320 | 1/1974 | Dye | 128/221 |
| 3,893,445 | 7/1975 | Hofsess | 128/754 |
| 4,314,565 | 2/1982 | Lee | 128/754 X |

FOREIGN PATENT DOCUMENTS

| | | | |
|---|---|---|---|
| 19104 | 11/1980 | European Pat. Off. | 128/754 |
| 1267960 | 6/1961 | France | 128/754 |

OTHER PUBLICATIONS

Hallac, Surgery, Apr. 1962, pp. 515–517.

Primary Examiner—Kyle L. Howell
Assistant Examiner—John C. Hanley
Attorney, Agent, or Firm—James R. Haller

[57] ABSTRACT

A biopsy needle having a cannula with a sharpened distal end and a stylet received coaxially in the cannula and having a sharpened distal end protruding from the distal end of the cannula. The distal ends of the stylet, the cannula, or both, are provided with particular cutting edge configurations enabling the needle to more readily penetrate bone.

9 Claims, 9 Drawing Figures

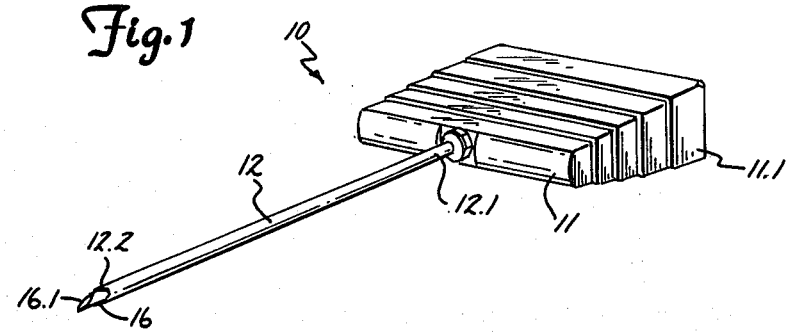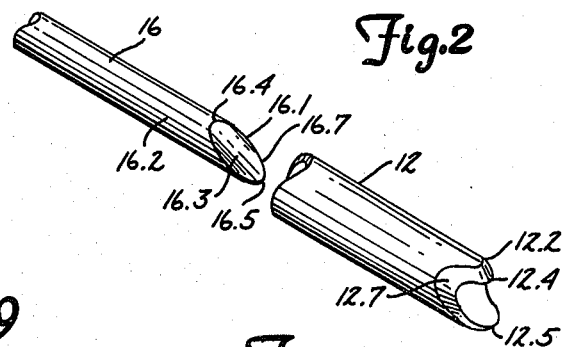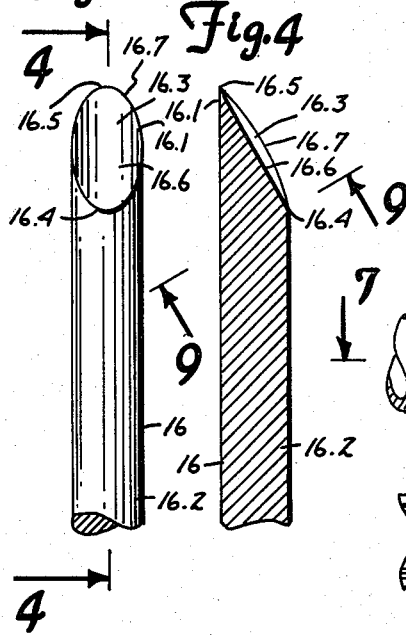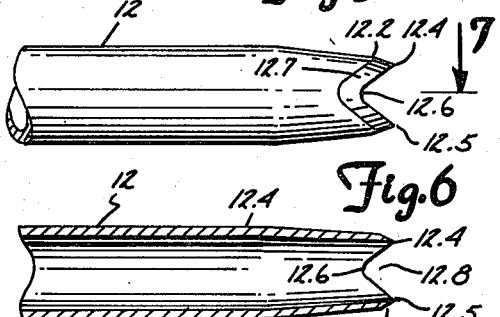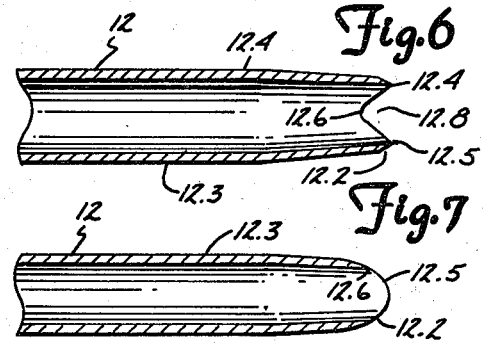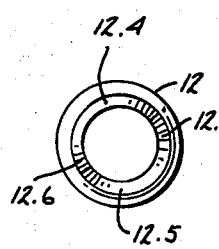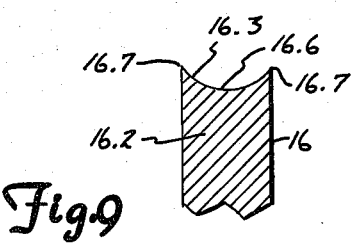

BIOPSY NEEDLE

TECHNICAL FIELD

The invention relates to the field of medical instruments, and more particularly to those instruments employed in biopsy procedures.

BACKGROUND ART

A typical biopsy needle comprises a hollow cannula having a sharpened distal end and a stylet that is received coaxially within the cannula, the stylet having a sharpened distal end that protrudes from the distal end of the cannula. The stylet and cannula commonly are releasably joined at or near their proximal ends. In bone marrow biopsy procedures, the cannula and stylet are forced with great pressure through the outer, hard layer of a marrow containing bone such as a hip bone. Once the softer, internal region of the bone is reached, the stylet may be withdrawn and a specimen is obtained by advancing the cannula itself further into the bone. Perhaps the greatest difficulty in bone marrow biopsy procedures is the step of penetrating the hard, outer layer of the bone in a controllable manner. Stylets and cannulas have been designed with various sharpened distal ends to facilitate bone penetration, and representative of these are the stylets and cannulas shown in U.S. Pat. Nos. 2,919,692, 2,426,535, 3,598,108, and 4,256,119. There is yet a need for a biopsy needle having stylet and cannula tips that can more readily penetrate bone.

DISCLOSURE OF INVENTION

The invention relates to a biopsy needle that can readily penetrate the hard outer surface of a marrow-containing bone. The invention in one embodiment relates to a biopsy needle having a cannula with a sharpened distal end and a stylet received coaxially in the cannula and having a sharpened distal end protruding from the distal end of the cannula. The sharpened distal end of the stylet is characterized by including an oblique concave face forming a rounded trough extending at an acute angle to, and intersecting, the axis of the stylet. In another embodiment, the invention relates to a biopsy needle in which the cannula terminates distally in a plurality of distally extending, axially coextensive, rounded lobes having distally sharpened edges forming a continuously curved, sinuous cutting edge. In the preferred embodiment, a biopsy needle is provided with a cannula having a distal end including a plurality of distally extending, axially coextensive, rounded lobes having distally sharpened edges, and a stylet received coaxially in the cannula and having a sharpened distal end protruding from the distal end of the cannula. The distal end of the stylet includes an oblique, concave face forming a rounded trough extending at an acute angle to, and intersecting, the axis of the stylet. The distal end of the stylet preferably protrudes a sufficient distance beyond the sharpened end of the cannula to permit the stylet to substantially completely penetrates the hard, outer bony layer of a marrow-containing bone before the cannula engages the bone surface.

BRIEF DESCRIPTION OF DRAWINGS

FIG. 1 is a perspective view of a bone marrow needle of the invention;

FIG. 2 is an exploded, broken-away view of the distal end of the device shown in FIG. 1;

FIG. 3 is a broken-away side view of the distal end of a stylet of the invention;

FIG. 4 is a broken-away, cross-sectional view taken along line 4—4 of FIG. 3;

FIG. 5 is a broken-away side view of the distal end portion of a cannula, shown also in FIG. 2;

FIG. 6 is a view similar to that of FIG. 5, but shown in cross-section;

FIG. 7 is a cross-sectional view taken along line 7—7 of FIG. 5;

FIG. 8 is an end view of the cannula of FIGS. 5-7; and

FIG. 9 is a broken-away, cross-sectional view taken along line 9—9 of FIG. 4.

BEST MODE FOR CARRYING OUT THE INVENTION

The biopsy needle shown in FIG. 1 is designated generally as (10) and includes a cannula (12) and a stylet (16) received coaxially within the cannula. As depicted, the proximal end (12.1) of the cannula is attached to a handle (11), and the proximal end (not shown) of the stylet is connected to a second handle (11.1) which in turn is releasably attached to and interconnects with the handle (11) so that the sharpened end (16.1) of the stylet protrudes from the sharpened end (12.2) of the cannula. The handles (11) and (11.1) are described in greater detail in copending patent application Ser. No. 255,048 filed Apr. 17, 1981. The means for attachment of the proximal ends of the cannula and stylet are unimportant to the instant invention, and suitable other means are shown, for example, in U.S. Pat. No. 3,598,108, the teachings of which are incorporated herein by reference.

A stylet of the invention, designated (16) is shown in FIGS. 2-4 and 9, and comprises a straight shank (16.2) that is desirably circular in cross-section. The solid distal end (16.1) of the stylet is beveled at an acute angle to the axis of the stylet to form an oblique face (16.3) extending across the width of the stylet shank. The face (16.3) extends from a point (16.4) along the length of the stylet adjacent but spaced from its tip, to the tip of the stylet. The face is concave; that is, it forms a trough extending between the point (16.4) and the tip (16.5) of the stylet, the trough extending at an acute angle to and intersecting the axis of the stylet. As shown best in FIG. 9, the trough is desirably circular in cross-section, and is formed on a diameter that is preferably about one and one-half to four times the diameter of the shank (16.2). If desired, the face (16.3) may also be made slightly concave in the transverse direction as well, providing the face with a recessed configuration that is generally spherical or ellipsoidal. In the preferred embodiment, the face (16.3) is concave with respect to an axis extending at an acute angle to, and intersecting, the axis of the stylet, the trough thus defined having a generally circular configuration when viewed along its axis, as in FIG. 9. The acute angle formed between the center (16.6) of the trough and the axis of the stylet desirably is not greater than about 45°, and preferably is in the range of about 30° or less.

The intersection between the face (16.3) and the outer surface of the stylet defines a sharp cutting edge (16.7) that is extremely effective in penetrating hard bone as will be described further below.

The end of the stylet can be readily formed by first beveling its distal end with a grinding wheel or the like to form a flat face at an angle to the axis, and then further grinding the flat face to provide the rounded trough as shown best in FIG. 9. The cutting edge (16.7) thus formed may be additionally sharpened through honing procedures employing fine grit abrasives.

The cannula (12) preferably is in the form of a smooth, hollow tube of circular cross-section throughout the majority of its length, the walls of the tube being designated (12.3) in FIGS. 6 and 7. As further noted in the drawing, the walls adjacent the distal end (12.2) of the cannula taper inwardly slightly from a point, designated (12.4) in FIG. 6, spaced a short distance from the sharpened end of the cannula. The distal end (12.2) of the cannula is provided with distally extending, distally coextensive lobes (12.4) and (12.5). The embodiment shown on the drawing has two such opposing lobes on opposite sides of the axis of the cannula. As shown best in FIG. 7, the lobes are gently rounded, and the edges thereof merge into one another as shown at (12.6) in the drawing. If the cannula were to be axially split and unrolled, the distal edge of the cannula formed by the lobes (12.4, 12.5) and the portions (12.6) between the lobes would form a generally sinusoidal curve. As shown best in FIG. 5, the distal end of the cannula may be appropriately ground, as shown at (12.7), to render the continuous, sinuous distal edge of the cannula extremely sharp. The lobes (12.4, 12.5) are axially coextensive, and, as depicted, the stylet preferably is provided with lobes on opposed sides of its axis in a symmetrical manner. If desired, three or more lobes may be employed rather than the two lobes as depicted in the drawing, but the embodiment having two lobes is preferred. The distal end of the stylet, when inserted in the cannula, protrudes from the cannula's distal end, the opening at the distal end of the cannula fitting snugly but slidably about the periphery of the stylet so that the outer surfaces of the stylet and cannula, in effect, merge into one another.

The distal end of the cannula may be formed as described above by grinding a rounded groove in the distal end of the cannula transversely of its axis (as shown at 12.8 in FIG. 6), and thereafter grinding or honing the outer periphery of the cannula at its distal end (as shown at 12.7 in FIG. 5) to provide the cannula with a continuous, generally sinuous sharpened edge.

When the stylet and cannula have been attached as shown in FIG. 1, the tip (16.5) of the stylet desirably protrudes from the lobes (12.4, 12.5) of the cannula by a distance approximating the thickness of the exceedingly hard layer of marrow-containing bone; that is, by a distance in the range of about 1 to about 2 mm.

The ability of the stylet and cannula described above to cut through hard materials was compared with that of a commercial bone marrow biopsy needle. The commercial needle employed a stylet having an oblique, flat face formed at its distal end at an acute angle to its axis. The distal cutting edge of the cannula similarly was formed on a plane biased at an acute angle to the axis thereof. Since the hardness of actual bone specimens varies greatly, a sheet of one-eighth inch thick polycarbonate plastic was selected as the test material to simulate bone. The biopsy needle shown in the drawing was oriented in a direction normal to the plane of the polycarbonate sheet, the point of the instrument was forced against the sheet with a pressure of 32 pounds, and the biopsy needle was rotated about its axis back and forth to simulate the motions of a surgeon when penetrating bone in an actual biopsy procedure. The penetration time was found to be 25 seconds. The experiment was repeated with a needle identical to that shown in the drawing except that the cannula was provided with three equally spaced, rounded, sharpened lobes about its distal periphery rather than the two opposed lobes shown in the drawing. Penetration time was found to be 28 seconds. Finally, the commercial needle described above was also subjected to the test, and the penetration time was found to be 73 seconds.

A second similar test procedure was performed utilizing the following needle configurations:

(a) The commercial cannula and stylet described above;

(b) The cannula of the commercial needle and the stylet shown in the attached drawing.

(c) The stylet and cannula shown in the attached drawing.

Each needle was forced against the polycarbonate sheet at an initial pressure of 30 pounds, and the amount of time, in seconds, for the stylet to penetrate the sheet was recorded. The pressure was then increased to 40 pounds, and the time in seconds required for penetration of the cannula through the sheet was recorded. The following results were obtained:

| | PENETRATION TIMES | | |
|---|---|---|---|
| CONFIG-URATION | STYLET PENETRA-TION, SECONDS | CANNULA PENE-TRATION, SECONDS | TOTAL PENETRA-TION, STYLET AND CANNULA, SECONDS |
| A | 25 | 35 | 60 |
| B | 17 | 35 | 52 |
| C | 17 | 13 | 30 |

As shown by the above data, the stylet and cannula of the invention individually are capable of penetrating hard surfaces much more readily than the commercial stylet and cannula described above, and the stylet and cannula of the invention preferably are employed together in a biopsy needle.

The cannula of the invention also may find utility in soft tissue biopsy procedures as well. The rounded, sharpened lobes at the distal end of the cannula are axially coextensive, and hence provide no axially displaced leading edge or point about which rotation may occur in an eccentric fashion. The coextensive lobes provide a smooth cutting action when the cannula is rotated about its axis in a biopsy procedure, and the sharpened distal end of the cannula proceeds smoothly and axially into the tissue to provide a substantially undistorted tissue specimen.

While a preferred embodiment of the present invention has been described, it should be understood that various changes, adaptations, and modifications may be made therein without departing from the spirit of the invention and the scope of the appended claims.

What is claimed is:

1. In a biopsy needle comprising a hollow cannula with a sharpened distal end and a stylet coaxially received in the cannula and having a sharpened solid distal end protruding from the distal end of the cannula, the improvement wherein the sharpened distal end of the stylet includes an oblique, concave face forming a trough extending at an acute angle to, and intersecting, the axis of the stylet.

2. The biopsy needle of claim 1 wherein the stylet is circular in cross-section and wherein the trough, taken in cross-section along its length, defines generally a segment of a circle having a diameter from about one and one-half to about four times the diameter of the stylet.

3. The biopsy needle of claim 1 wherein the sharpened end of the cannula terminates in a plurality of distally extending, axially coextensive, rounded lobes having distally sharpened edges.

4. The biopsy needle of claim 3 in which the lobes are two in number and are opposed.

5. The biopsy needle of claim 3 in which the sharpened end of the cannula provides a smoothly curved, sinuous, distally sharpened continuous cutting edge.

6. The biopsy needle of claim 3 wherein the cannula has an inner bore narrowing at its distal end to closely circumscribe the stylet adjacent but spaced proximally from the sharpened distal end of the stylet.

7. A biopsy needle comprising a hollow cannula with a sharpened distal end and a stylet coaxially received in the cannula and having a sharpened solid distal end protruding from the distal end of the cannula, the distal end of the stylet including an oblique, concave face forming a trough extending at an acute angle to the stylet axis and intersecting said axis, the stylet having an outer surface intersected by said face with said intersection defining a sharp cutting edge.

8. In a biopsy needle comprising a hollow cannula with a sharpened distal end and a stylet coaxially received in the cannula and having a sharpened solid distal end protruding from the distal end of the cannula, the improvement wherein the sharpened distal end of the stylet includes a single face formed at an oblique angle to the axis of the stylet, the face being concave and forming a trough extending at an acute angle to, and intersecting the axis of the stylet.

9. A biopsy needle comprising a hollow cannula with a sharpened distal end and a stylet coaxially received in the cannula and having a sharpened distal end protruding from the distal end of the cannula, the distal end of the stylet including a single face extending at an acute angle to the stylet axis and being concave to provide a trough extending at an acute angle to and intersecting said axis, the cannula terminating distally in a pair of opposed, distally extending, axially coextensive, rounded lobes having distally sharpened edges and providing a smoothly curved, sinuous, distally sharpened continuous cutting edge.

* * * * *